United States Patent [19]

Pfoh et al.

[11] Patent Number: 5,400,379
[45] Date of Patent: Mar. 21, 1995

[54] MULTI-SLICE X-RAY CT USING A DETECTOR MASK

[75] Inventors: Armin H. Pfoh, New Berlin; Hui Hu, Waukesha; Michael F. Gard, New Berlin, all of Wis.

[73] Assignee: General Electric Company, Milwaukee, Wis.

[21] Appl. No.: 201,916

[22] Filed: Feb. 25, 1994

[51] Int. Cl.⁶ ............................................. A61B 6/00
[52] U.S. Cl. ................................. 378/19; 378/4; 378/154
[58] Field of Search ............... 378/4, 19, 145, 149, 378/147, 154

[56] References Cited

U.S. PATENT DOCUMENTS

| | | | |
|---|---|---|---|
| 4,187,430 | 2/1980 | Schmidt | 378/19 |
| 4,193,001 | 3/1980 | Liebetruth | 378/19 |
| 4,995,107 | 2/1991 | Klingerbeck | 378/19 X |
| 5,191,600 | 3/1993 | Vincent et al. | 378/19 X |
| 5,323,439 | 6/1994 | Nobuta et al. | 378/4 X |

*Primary Examiner*—David P. Porta
*Attorney, Agent, or Firm*—Quarles & Brady

[57] ABSTRACT

An imaging system includes a linear detector array which measures x-rays passing through a patient from an x-ray source. A mask disposed over the detector array has staggered segments that block x-rays and divide the detector array into a pair of slice planes. Signals from the detector elements receiving x-rays in respective ones of the two slice planes are used to separately reconstruct a slice image for each of the two slice planes.

7 Claims, 2 Drawing Sheets

MULTI-SLICE X-RAY CT USING A DETECTOR MASK

BACKGROUND OF THE INVENTION

The present invention relates to computed tomography (CT) imaging apparatus; and more particularly, to the acquisition of multiple slices with a linear detector array.

In a computed tomography system, an x-ray source projects a fan-shaped beam which is collimated to lie within an x-y plane of a Cartesian coordinate system, termed the "imaging plane". The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional "3rd generation" CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views made at different angular orientations during one revolution of the x-ray source and detector. A conventional "4th generation" CT system is similar, except the detector array is a stationary ring that surrounds the patient and only the x-ray source rotates during the scan.

The scan data is processed to construct an image that corresponds to a two dimensional slice taken through the object. The prevailing method for reconstructing an image is referred to in the art as the filtered backprojection technique. This process converts the attenuation measurements from a scan into integers called "CT numbers" or "Hounsfield units", which are used to control the brightness of a corresponding pixel on a cathode ray tube display.

In order to acquire multiple slices during a single revolution of the gantry, it is common practice to provide a 2-dimensional detector array which has two or more rows of separate detector elements disposed along the Z dimension. The change from a linear to a 2-dimensional detector array requires a major alteration of the detector, the data acquisition system, the data communication and transfer system, as well as the data and image processing system. Such changes are costly, and once made, there is no easy way to revert back to a single slice data acquisition.

SUMMARY OF THE INVENTION

The present invention is an improvement for a computed tomography system using a linear detector array which enables multiple slices to be acquired during a single revolution of the gantry. More specifically, the invention includes a mask which is positioned between the x-ray source and the linear detector array and includes segments which are staggered along the Z dimension to block x-rays from reaching portions of each detector element. As a result, the detector array elements are divided into subsets of elements which gather attenuation data in different slice planes through the object during a single gantry revolution, and this data may be separately processed to produce an image through each slice plane.

A general object of the invention is to enable a CT system to acquire multiple slices using a linear detector array. The mask effectively divides the set of detector array elements into subsets of elements that see x-rays in different slice planes. In a two-slice embodiment, for example, alternate halves of successive elements in the detector array are blocked by the staggered mask segments. As a result, one half of the detector array elements measure x-ray attenuation in one slice plane and the other half measure x-ray attenuation in an adjacent slice plane. Signals from these two subsets of elements are separately processed to produce two slice images.

Another object of the invention is to minimize the changes required to produce multiple slice images. In addition to the use of a mask, the only other change required is in the handling of the acquired attenuation data so that separate images are reconstructed. No changes need me made in the digital acquisition system or image reconstruction processor.

A more specific object of the invention is to enable single slice or multiple slice modes of operation with minimal changes to the CT system. By inserting or removing the mask and switching the data handling, the CT system is easily converted between single slice and multi-slice modes of operation. The detector array and front end electronics need not be changed and the same image processing hardware is used for either mode.

DETAILED DESCRIPTION OF THE INVENTION

Figure 1:
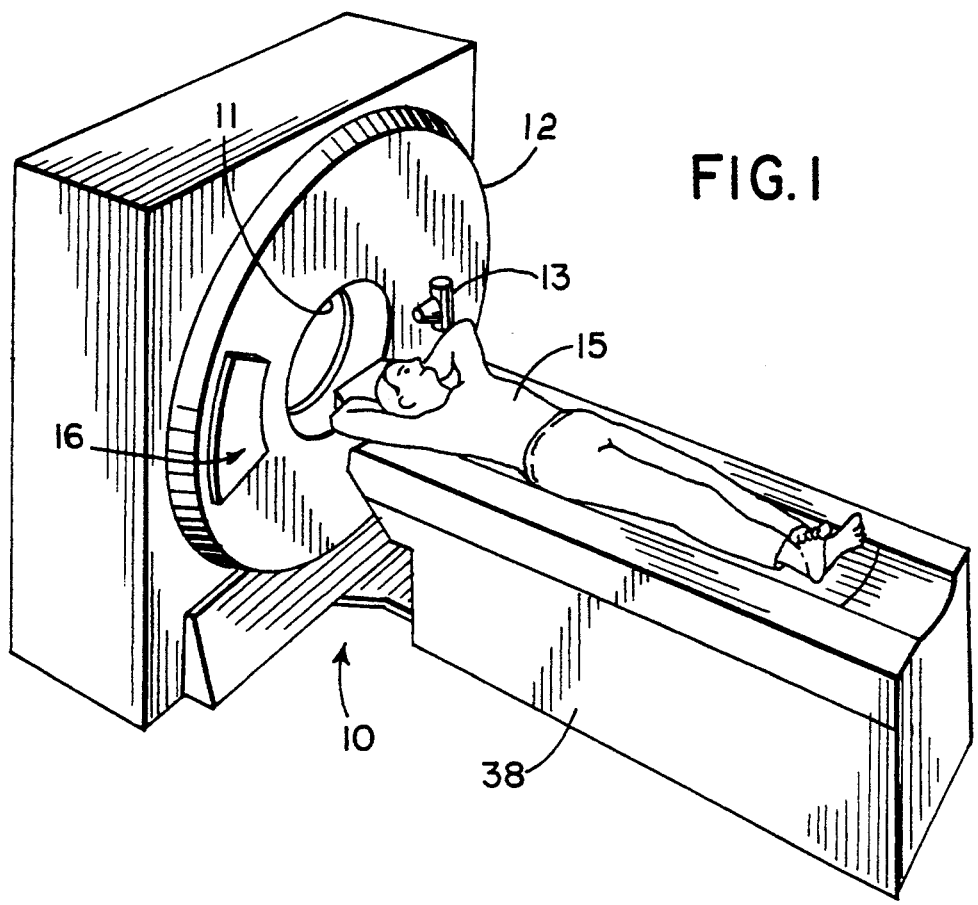
FIG. 1 is a pictorial view of a CT imaging system in which the present invention may be employed.
Figure 2:
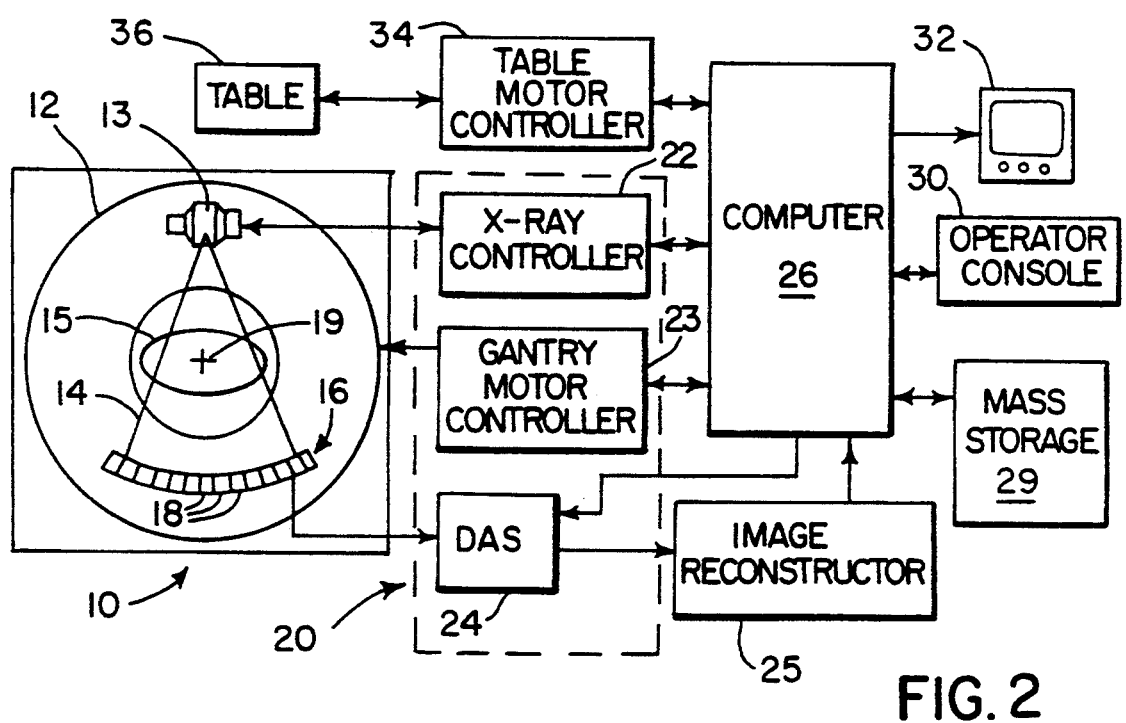
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a fan beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog scan data from detector elements 18 and converts the data to digital signals for subsequent processing. An image reconstructor 25, such as a conventional array processor, receives sampled and digitized x-ray scan data from the DAS 24 and performs high speed image reconstruction as will be described in more detail below. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 4A:
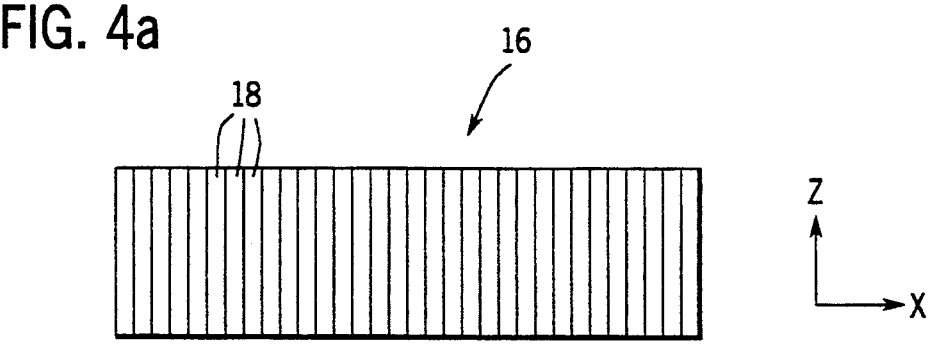
FIG. 4A is a plan view of a linear detector array and FIG. 4B is a mask which overlies this linear detector array to practice the present invention.

During a scan a series of views of the patient is acquired as the gantry 12 rotates about the axis 19. Each view is a set of x-ray scan data values which indicate the number of x-ray photons sensed by the respective detector elements 18. As shown in FIG. 4a, the elements 18 in the detector array 16 are disposed linearly in an arc which extends along an x-axis, and each element 18 has a dimension that extends along the z-axis. The z-axis is the same direction as the center of rotation 19 and is a measure of the location of the slice image to be produced. Each view of scan data values produced by the detector array 16 is digitized by the DAS 24 and applied to the image reconstructor 25. If there are 852 separate detector elements 18 each view is comprised of 852 separate digital scan data values.

Figure 3:
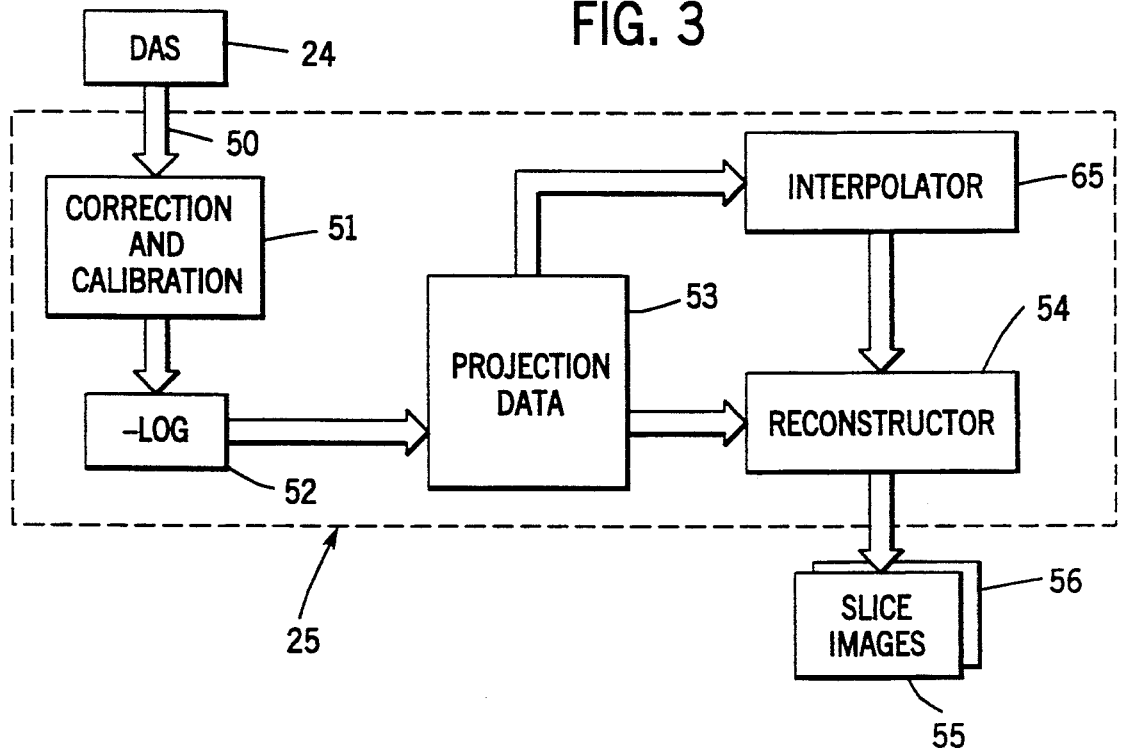
FIG. 3 is a block schematic diagram of the image reconstructor that forms part of the CT imaging system of FIG. 2.

Referring to FIG. 3, each view of scan data is received at input 50 and processed at 51 to correct for various well known errors such as variations in detector and channel gains. The corrected data is next log adjusted at 52 by taking the negative of its logarithm to provide a projection profile P which indicates the amount of attenuating material in the patient 15 along the x-ray beam associated with each detector element 18. This profile data is stored in memory 53, and in the single slice mode of operation, all the stored profile data is read out and applied to a reconstructor 54. The reconstructor 54 filters the projection data P and back projects each view to produce a slice image 55.

Figure 4B:
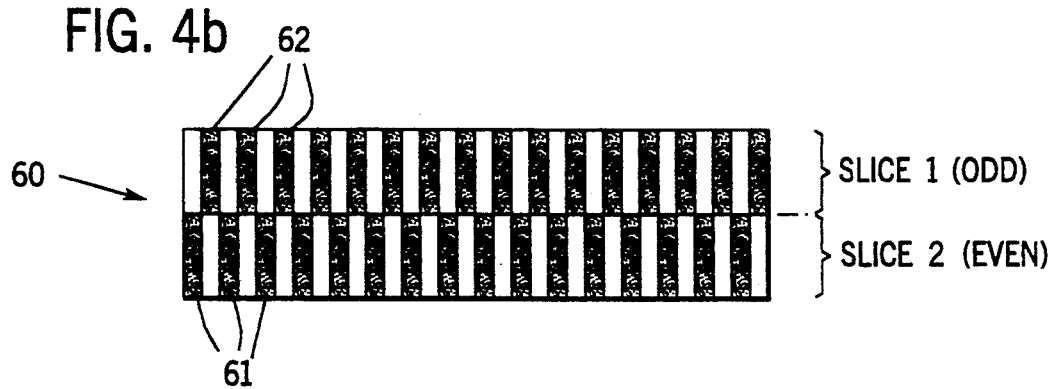

The preferred embodiment of the present invention enables this same CT system with minimal modifications to produce two slice images 55. The first modification is the use of a mask 60 which is positioned over the detector array 16 to selectively block x-rays from reaching detector elements 18. This mask 60 is shown in FIG. 4b and it includes segments 61 and 62 which are staggered along the Z dimension to block x-rays from reaching one half of each detector element 18. As a result, the odd numbered detector elements 18 see x-rays in a first slice plane and the even numbered detector elements 18 see x-rays in a second slice plane.

Referring again to FIG. 3, the signals from all the detector elements 18 are digitized and processed by the DAS 24 as described above. The scan data is corrected at 51, converted to projection profile data at 52, and stored in memory 53 also as described above. However, rather than applying all the projection profile data 53 to the reconstructor 54 as described above, only the odd numbered detector values are read from the memory 53 and applied to an interpolator 65. The interpolator 65 interpolates between each successive pair of odd numbered detector values to create interpolated projection data values that fill out the projection profile values normally occupied by the even numbered detector values. The resulting projection profile data is applied to the reconstructor 54 which produces a first slice image 55.

The even numbered detector values of projection data are then read from the memory 53 and applied to the interpolator 65. The projection profile values normally occupied by the odd numbered detector values are calculated by interpolating between successive pairs of even numbered detector values and the complete projection profile is filtered and back projected by reconstructor 54 to form a second slice image 56. Each view of acquired data is thus separated into two projection profiles and back projected to form two separate slice images 55 and 56.

Since the in-plane sampling density is reduced by a factor of two when the multi-slice mode of operation is employed, aliasing artifacts will degrade the image quality. This degradation can be minimized, however, by changing the CT system from a "quarter detector offset" (QDO) to a "half detector offset" (HDO). Offset here means the distance between the point of intersection of a line passing through the x-ray tube focal spot and the system iso-center 19 with the detector array and the next closest center of an individual detector cell 18. For QDO this distance is 0.25 of the detector pitch, and it is 0.5 for HDO. Maintaining the QDO alignment when the masked detector is used according to the present invention, causes a highly non-uniform in-plane sampling. Changing to the HDO alignment produces a more uniform sampling pattern for the masked detector configuration. The change from QDO to HDO can be achieved in two ways: mechanically move the detector array along x by 0.25 detector channels, or change the x-ray tube focal spot position in order to accomplish the same relative change in geometry. Either case will accomplish a higher sampling uniformity and therefore reduce the severity of the aliasing artifact when the present invention is employed. It appears that the focal spot dislocation approach is the more desirable one, since it is more cost effective and it makes it easier to change from the single slice to dual slice mode and visa versa. The focal spot relocation can be realized in a controlled and reversible manner via magnetic or electrostatic deflection of the x-ray source electron beam.

It should be apparent to those skilled in the art that variations from the preferred embodiment are possible without departing from the spirit of the invention. For example, the mask segments may be staggered in such a way as to divide the linear detector elements into three or more subsets disposed in three or more separate slice planes. While three or more separate slice images may be reconstructed from data acquired during a single revolution of the gantry, the image quality will be further reduced. Also, while a 3rd generation CT system is described herein, the invention is equally applicable to a 4th generation system in which the detector array is a stationary ring of linearly disposed detector elements and only the x-ray source is revolved by the gantry.

We claim:

1. A computed tomography imaging system which comprises:

a detector array comprised of a plurality of detector elements aligned linearly in a path disposed in a plane that intersects a central axis;

an x-ray source for producing x-rays which impinge on the detector array elements after passing through a patient disposed along the central axis;

a mask positioned between the x-ray source and the detector array, the mask having a plurality of segments positioned over successive detector elements in the detector array to block x-rays from reaching a portion of each detector element, the segments being staggered to define a plurality of slice planes disposed along the direction of the central axis by establishing subsets of said plurality of detector elements which detect x-rays in each of said plurality of slice planes; and an image reconstructor coupled to the detector array to receive scan data therefrom which indicates the x-rays impinging on each detector element, the image reconstructor including means for reconstructing a separate slice image from the scan data produced by each of said subsets of detector elements.

2. The computed tomography imaging system as recited in claim 1 in which the mask segments are staggered to define two slice planes and each of the subsets of detector elements is comprised of alternate ones of the successive detector elements in the detector array.

3. The computed tomography imaging system as recited in claim 1 in which the image reconstructor includes an interpolator which produces data by interpolating between the scan data produced by each subset of detector elements.

4. The computed tomography imaging system as recited in claim 3 in which the data produced by the interpolator is employed in a reconstructor that produces the slice image by back projecting said data.

5. The computed tomography imaging system as recited in claim 1 in which the x-ray source is mounted on a gantry that revolves the x-ray source around the central axis to produce scan data from a plurality of different angles through the patient.

6. The computed tomography imaging system as recited in claim 5 in which the detector array is also mounted to the gantry and revolves around the patient with the x-ray source.

7. The computed tomography imaging system as recited in claim 1 in which the x-ray source includes means for altering detector offset by relocating a focal spot in the x-ray source.

* * * * *